United States Patent
Wada et al.

(10) Patent No.: US 8,388,588 B2
(45) Date of Patent: Mar. 5, 2013

(54) URINE RECEIVER

(75) Inventors: Ichiro Wada, Kagawa-ken (JP); Miou Suzuki, Kagawa-ken (JP); Naruto Matsushita, Kagawa-ken (JP); Kiyoshi Toda, Tokyo (JP); Yuichi Hirai, Tokyo (JP); Masaho Hayashi, Tokyo (JP); Hiroshi Uematsu, Tokyo (JP); Toshihiko Uenishi, Fukuoka (JP)

(73) Assignee: Unicharm Corporation, Ehime (JP)

( * ) Notice: Subject to any disclaimer, the term of this patent is extended or adjusted under 35 U.S.C. 154(b) by 225 days.

(21) Appl. No.: 12/758,356

(22) Filed: Apr. 12, 2010

(65) Prior Publication Data

US 2010/0198172 A1  Aug. 5, 2010

Related U.S. Application Data

(63) Continuation of application No. 11/457,304, filed on Jul. 13, 2006, now Pat. No. 7,695,460.

(30) Foreign Application Priority Data

Jul. 14, 2005 (JP) ................. 2005-205737
Jul. 10, 2006 (JP) ................. 2006-188783

(51) Int. Cl.
*A61F 5/44* (2006.01)
(52) U.S. Cl. ........ 604/354; 604/317; 604/319; 604/321; 604/322; 604/326; 604/327; 604/346; 604/347; 604/349; 604/351; 604/355
(58) Field of Classification Search .......... 604/349, 604/351, 353, 355
See application file for complete search history.

(56) References Cited

U.S. PATENT DOCUMENTS

| | | | |
|---|---|---|---|
| 640,666 | A | 1/1900 | Knapp |
| 4,631,061 | A | 12/1986 | Martin |
| 4,747,166 | A | 5/1988 | Kuntz |
| 4,798,603 | A | 1/1989 | Meyer et al. |
| 5,002,541 | A | 3/1991 | Conkling et al. |
| 5,681,297 | A | 10/1997 | Hashimoto et al. |
| 5,911,222 | A | 6/1999 | Lawrence et al. |
| 7,220,250 | B2 | 5/2007 | Suzuki et al. |
| 2004/0236292 | A1 | 11/2004 | Tazoe et al. |

FOREIGN PATENT DOCUMENTS

| | | |
|---|---|---|
| EP | 1457178 A1 | 9/2004 |
| EP | 1486184 | 12/2004 |
| EP | 1520566 | 4/2005 |
| JP | 2174846 A1 | 7/1990 |
| JP | 6014741 Y2 | 4/1994 |
| JP | 7239990 A1 | 9/1995 |
| JP | 11295250 A1 | 10/1999 |
| JP | 2004-267517 | * 9/2004 |
| JP | 2004267517 A1 | 9/2004 |
| JP | 2006026108 A1 | 2/2006 |
| WO | 20071008745 A1 | 1/2007 |

OTHER PUBLICATIONS

EP Search Report for 06768204 issued May 27, 2010.

* cited by examiner

*Primary Examiner* — Tatyana Zalukaeva
*Assistant Examiner* — Ilya Treyger
(74) *Attorney, Agent, or Firm* — Lowe Hauptman Ham & Berner, LLP

(57) ABSTRACT

Here is disclosed a urine receiver. The urine receiver which collects urine of a wearer of the urine receiver under suction force has a container member provided with a bottom, a peripheral wall and flange. The container member has a suction tube which extends through the peripheral wall and has a urine suction port opening toward the interior of the container member and a urine evacuation port opening toward the exterior of the container member. The evacuation port is adapted to be connected to a connector of a urine suction means provided externally of the container member.

1 Claim, 16 Drawing Sheets

URINE RECEIVER

RELATED APPLICATIONS

The present application is a continuation of U.S. application Ser. No. 11/457,304 filed Jul. 13, 2006, and claims priority from Japanese Patent Application No. 2005-205737 filed Jul. 14, 2005 and Japanese Patent Application No. 2006-188783 filed on Jul. 10, 2006. The above listed applications are herein incorporated by reference in their entirety.

BACKGROUND OF THE INVENTION

The present invention relates generally to a urine receiver adapted to be used with an automatic urine disposal system for persons such as bedridden aged, bedridden patient and physically disabled persons for whom it is difficult to control timing of urination and/or to make a disposal of urine after discharged.

It is often difficult for those persons as have been described above to control a timing of urination and/or to make a disposal of urine after discharged, by one's own ability. As means for the urine disposal in such a case, automatic urine disposal systems have already been proposed. According to such automatic urine disposal systems of prior art, a urine receiver is put against a wearer's crotch around the urethral so that, upon occurrence of urination, urine is sucked by a suction pump so as to be guided into a urine reservoir. The suction pump evacuates the air within the urine reservoir and guides the urine together with the air from the urine receiver into the urine reservoir via a urine guide tube under a differential pressure generated between the urine reservoir and the atmospheric pressure.

According to Japanese Laid-Open Patent Application No. 2004-267517A, a urine receiver used in a combination with such an automatic urine disposal system comprises an air-impermeable outer sheet configured to have a square U-shape cross-section and a substantially rectangular planar shape filled with urine collecting material, a substantially air-impermeable topsheet placed upon the upper surface of the urine collecting material, a urine guide tube extending from a urine guide port formed in a bottom of the outer sheet to a urine reservoir and a suction pump adapted to guide urine from the receiver into the urine reservoir.

In the case of this urine receiver, the urine guide port to which the urine guide tube is connected is provided in the bottom side of the outer sheet filled with the urine collecting material. With such an arrangement, it has been difficult for the suction pump to evacuate the urine remaining in the urine collecting material along its peripheral region. And if the urine guide port is provided so as to reach the peripheral region, the urine guide tube connected to the urine guide port will be squeezed between the outer sheet and the topsheet. Consequentially, it is not easy to ensure that the topsheet and the outer sheet are sealed around the urine guide tube.

SUMMARY OF THE INVENTION

In view of the problems as described above, it is an object of the present invention to improve urine collecting features of the urine receiver of prior art.

According to the present invention, there is provided a urine receiver comprising a leak-proof container member, a suction part formed in the container member so as to extend outward through the container member and to be connected to a urine suction means provided externally of the container member, and a liquid-pervious sheet adapted to cover an opening of the container member wherein an amount of urine sucked into the container member through the liquid-pervious sheet under a negative pressure generated by the urine suction means is evacuated out from the container member via the suction part under the negative pressure.

The container member is a hollow structure having a length direction, a width direction and a thickness direction which are orthogonal one to another, and comprises a bottom and a peripheral wall rising in the thickness direction from the bottom so that the peripheral wall surrounds the bottom and the upper edge of the peripheral wall defines the opening, the liquid-pervious sheet covering the opening is attached to the upper edge and thereby the container member cooperates with said liquid-pervious sheet to form a urine suction space, the suction part has a urine suction port opening toward the urine suction space and a urine evacuation port opening toward the exterior of the urine suction space.

According to one embodiment, the container member is provided along the upper edge of the peripheral wall with a flange extending outward from the container member and the liquid-pervious sheet is attached to the upper surface of the flange.

According to another embodiment, the peripheral wall is formed with the urine evacuation port to which a urine guide tube of the urine suction means adapted to generate the negative pressure is connected.

According to still another embodiment, the suction part has a tubular urine guide member extending from the urine evacuation port toward the interior of the container member and the urine suction port has a space of 2 to 7 mm from any one of a part of the peripheral wall and a rib extending from the peripheral wall into the container member.

According to further another embodiment, the liquid-pervious sheet exhibits an air-permeability as specified by JIS L 1096, Section 6. 27. 1 in a range of 0 to 100 cc/cm$^2$/sec in a wet condition and in a range of 20 to 200 cc/cm$^2$/sec in a dried condition.

According to yet another embodiment, the liquid-pervious sheet contains rayon fiber of 40% by weight or higher.

According to an alternative embodiment, the container member is formed by thermoplastic synthetic resin, the liquid-pervious sheet contains in its region facing the flange thermoplastic synthetic resin material having a melting temperature substantially same as or lower than that of the container member, and the liquid-pervious sheet is attached to said flange by melting of the thermoplastic synthetic resin material.

According to another embodiment, the thermoplastic synthetic resin material is provided in a form of liquid-pervious nonwoven fabric made of thermoplastic synthetic fiber, the nonwoven fabric being placed underneath the liquid-pervious sheet and fixed to the upper edge so as to cover the opening wherein the air-permeability of the liquid-pervious sheet is statisfied by the combination of the liquid-pervious sheet and the nonwoven fabric placed thereupon.

According to still another alternative embodiment, the thermoplastic synthetic resin material is provided in a form of liquid-impervious film extending outward from the flange of the container member but not extending inward into the container member.

According to yet alternative embodiment, the container member is formed on the bottom with a plurality of protuberances extending in the thickness direction so as to come in contact with the liquid-pervious sheet from below and thereby to prevent the liquid-pervious sheet from bending toward the bottom.

According to further alternative embodiment, the container member is formed by soft elastic material, the length direction of the container member corresponds to the vertical direction of the urine receiver's wearer and the plurality of protuberances are formed in alignment with the length direction and the width direction.

According to a varied embodiment, the urine receiver includes an electrical sensor interposed between the urine receiver wearer's skin and the liquid-pervious sheet so as to detect a urination by the urine receiver's wearer.

According to another varied preferred embodiment, the electrical sensor is at least partially covered with a liquid-pervious sheet-like filter to prevent solid content of bodily discharges from coming in contact with the electrical sensor, a sheet-like spacer having a thickness of at least 0.7 mm and a plurality of through-holes each having a diameter of at least 2 mm is interposed between the electrical sensor and the filter, and the sheet-like spacer is substantially incompressible in the thickness direction.

According to still another varied embodiment, the urine receiver is provided along both side edges opposed to each other in the width direction with leak-proof barriers formed by a liquid-impervious sheet, each of the leak-proof barriers having an outer side edge as viewed in the width direction and opposite ends as viewed in the length direction fixed to the urine receiver and an inner side edge as viewed in the width direction left free from the urine receiver and being elastically stretchable/contractible in the length direction.

According to yet another varied embodiment, the container member has its outer surface covered with the liquid-impervious sheet and a portion of the liquid-impervious sheet extending outward from the container member is bonded to sheet materials extending on the inner surface of the container member and further extending outward from the container member.

According to further varied embodiment, the liquid-impervious sheet is formed by a thermoplastic synthetic resin film or a laminate sheet of the film and nonwoven fabric attached to the outer surface of the film.

According to the present invention, the suction part is formed integrally with the container member and the liquid-pervious sheet is attached to the upper edge of the peripheral wall of the container member. With such a unique arrangement, the liquid-pervious sheet can be easily and reliably attached to the upper edge and an air-tightness of the receiver can be also easily and reliably improved.

According to the embodiment of the present invention wherein the container member is formed with the flange, the liquid-pervious sheet and the container member can be more easily and reliably fixed to each other.

According to the embodiment of the present invention wherein the peripheral wall of the container member is provided with the urine evacuation port of the suction part, the urine guide tube of the urine suction means can be easily connected to this urine evacuation port.

According to the embodiment of the present invention wherein the urine suction port of the suction part is formed in the vicinity of the peripheral wall as well as the rib, even if the liquid-pervious sheet bows toward the interior of the container member, the liquid-pervious sheet does not get into the space defined between the urine suction port and the peripheral wall and/or the rib so as to choke up this port.

According to the embodiment of the present invention wherein the air-permeability of the liquid-pervious sheet is specified, upon activation of the suction pump included in the urine suction means, the desired negative pressure is quickly generated and thereby the urine can smoothly move into the container member.

The other embodiments of the present invention and advantageous functions as well as effects achieved thereby will be described in the following.

DETAILED DESCRIPTION OF THE PREFERRED EMBODIMENTS

Details of a urine receiver according to the present invention will be more fully understood from the description given hereunder in reference with the accompanying drawings.

Figure 1:
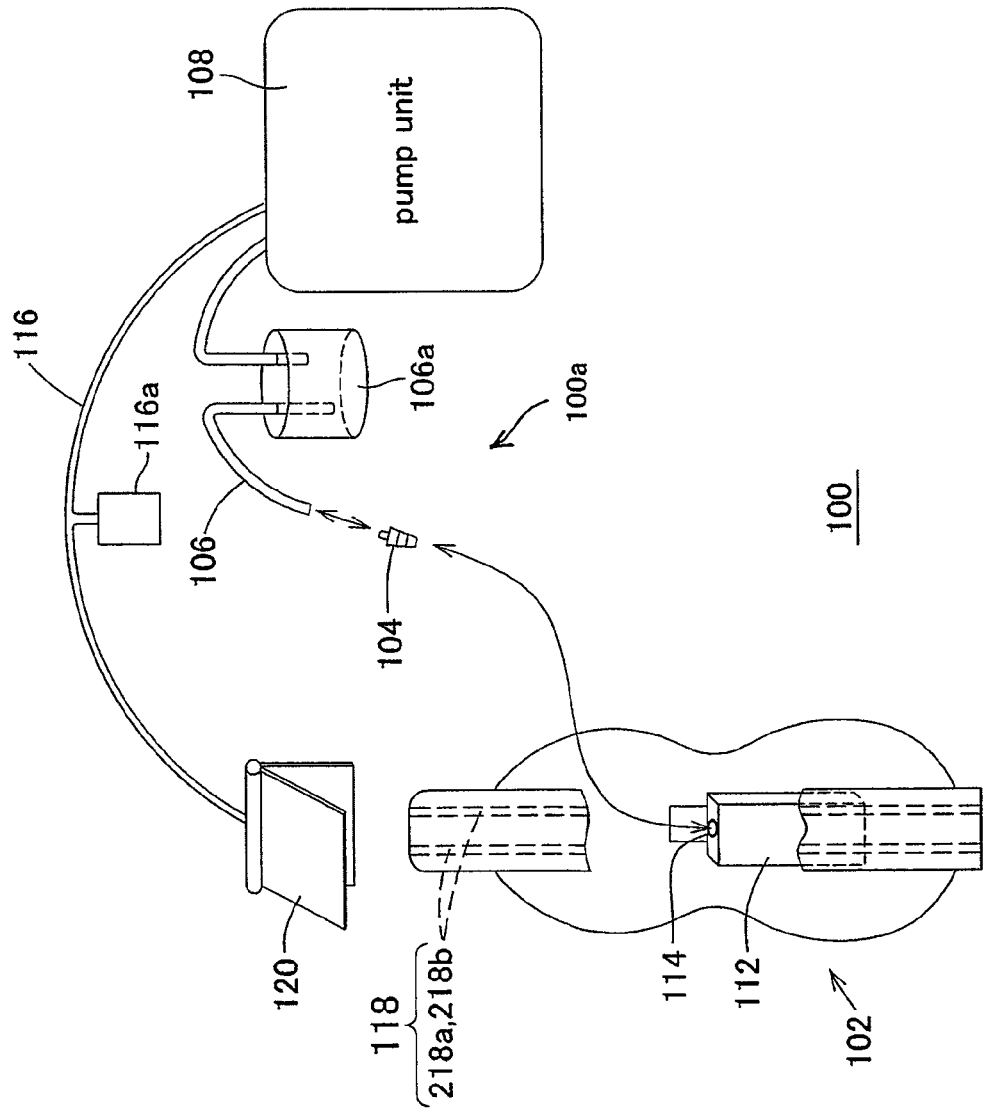
FIG. 1 is a schematic diagram illustrating a construction of an automatic urine disposal system including a urine receiver.

FIG. 1 is a diagram schematically illustrating a construction of an automatic urine disposal system 100 including a urine suction mechanism 100a to be combined with a urine receiver 102 according to the invention. While the urine receiver 102 has an inner side member facing the wearer's skin and an outer side member facing the wearer's clothes, the outer side member is shown as partially broken away.

The automatic urine disposal system 100 is adapted to collect urine discharged from the wearer (not shown) by the urine receiver 102 for disposal. The urine receiver 102 includes a tray-like container member 112 to face the wearer's skin in the vicinity of the urethral and to receive urine discharged while the automatic urine disposal system 100 includes the urine suction mechanism 100a comprising various components such as a joint member 104, a urine guide tube 106 and a pump unit 108.

The pump unit 108 comprises a urine reservoir 106a adapted to take over the amount of urine having been collected by the urine receiver 102 and to pool this, electric wiring 116 serving for an electrical connection of a urine sensor 118 provided on the urine receiver 102 for detection of urination to the pump unit 108, and a suction pump (not shown) adapted to be activated in response to a signal transmitted from the urine sensor 118 via the wiring 116. In the urine receiver 102, a peripheral wall of the container member 112 is formed with a urine evacuation opening 114 and the urine guide tube 106 is connected to this opening 114 by means of the joint member 104. The wiring 116 extending from the pump unit 108 is provided at its distal end with a clip 120 serving for electric connections of electrodes 218a, 218b (see FIG. 3) of the urine sensor 118 and others provided in the urine receiver 102 to the wiring 116. Such an automatic urine disposal system 100 detects a urination by the urine sensor 118 and the suction pump included in the pump unit 108 is activated in response to the detection signal. The pump unit 108 vacuums up air within the urine reservoir 106a so that the urine discharged from the wearer may be forcibly guided into the container member 112 and eventually collected into the urine reservoir 106a via the joint member 104 and the urine guide tube 106.

Figure 2:
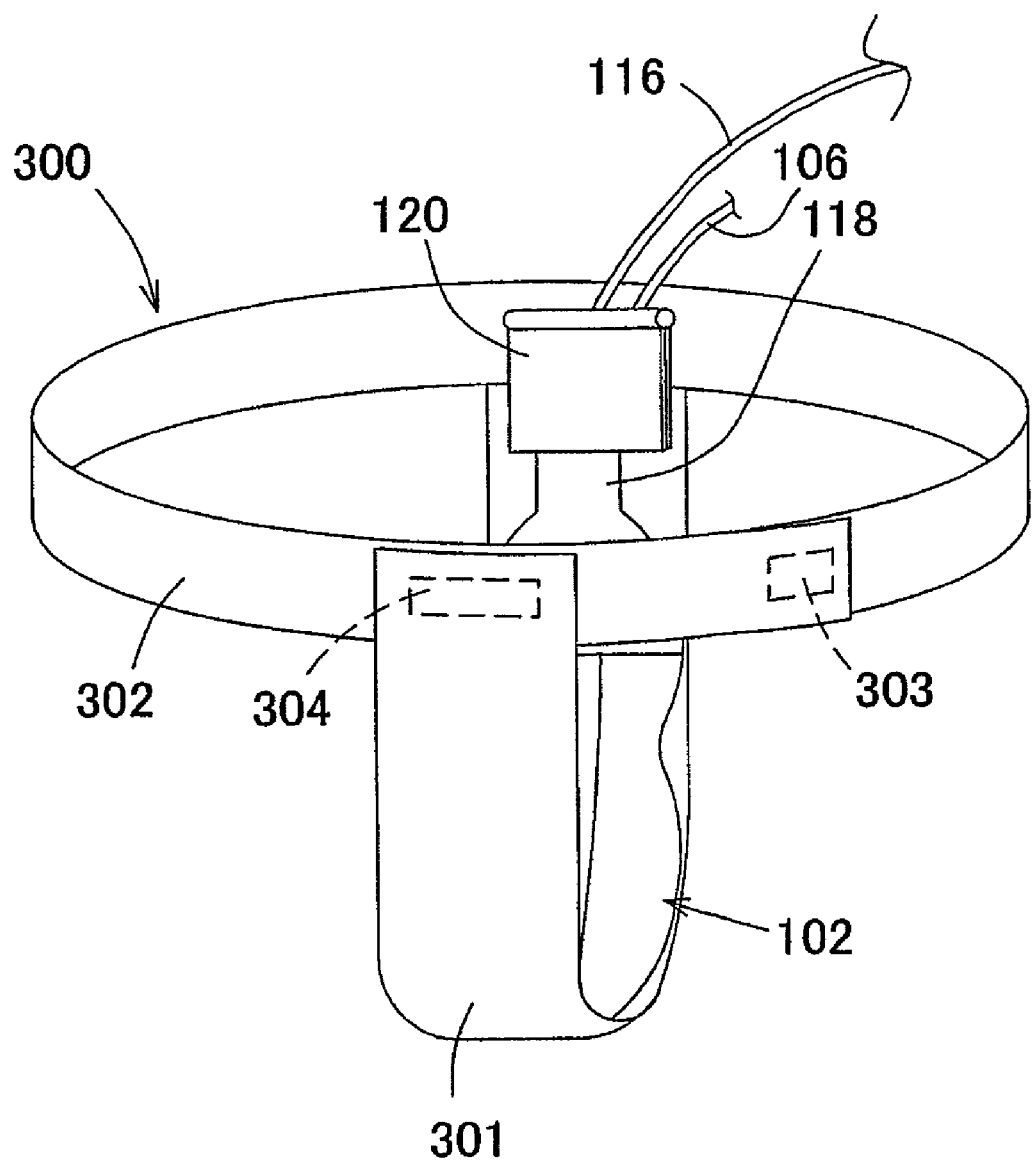
FIG. 2 is a diagram showing the urine receiver as put on a wearer.

FIG. 2 is a diagram exemplarily illustrating how to wear the urine receiver 102. The urine receiver 102 is fixed to the inner side of a crotch belt section 301 constituting a T-shaped belt 300 by means of, for example, a pressure-sensitive adhesive or a mechanical fastener known in a trade name of Magic Tape. Being put on the wearer's body, a major part of the container member 112 of the urine receiver 102 extends in the vertical direction of the wearer's body with the inner side facing the urethral and the skin extending therearound while a lower end of the container member 112 extends toward the anus so as to describe a gentle curve. In the T-shaped belt 300, longitudinally opposite ends of a waist belt section 302 are detachably connected to each other by a suitable connector means 303 such as a mechanical fastener while the crotch belt section 301 has end stitched together with the waist belt section 302 and the other end detachably connected to the waist belt section 302 by means of the mechanical fastener 304. It should be noted here that the chassis for the urine receiver 102 is not limited to the illustrated T-shaped belt and the other appropriate means such as the open- or pants-type diaper, the diaper cover or the pants for incontinent patient can be used as the chassis for the urine receiver 102.

Figure 3:
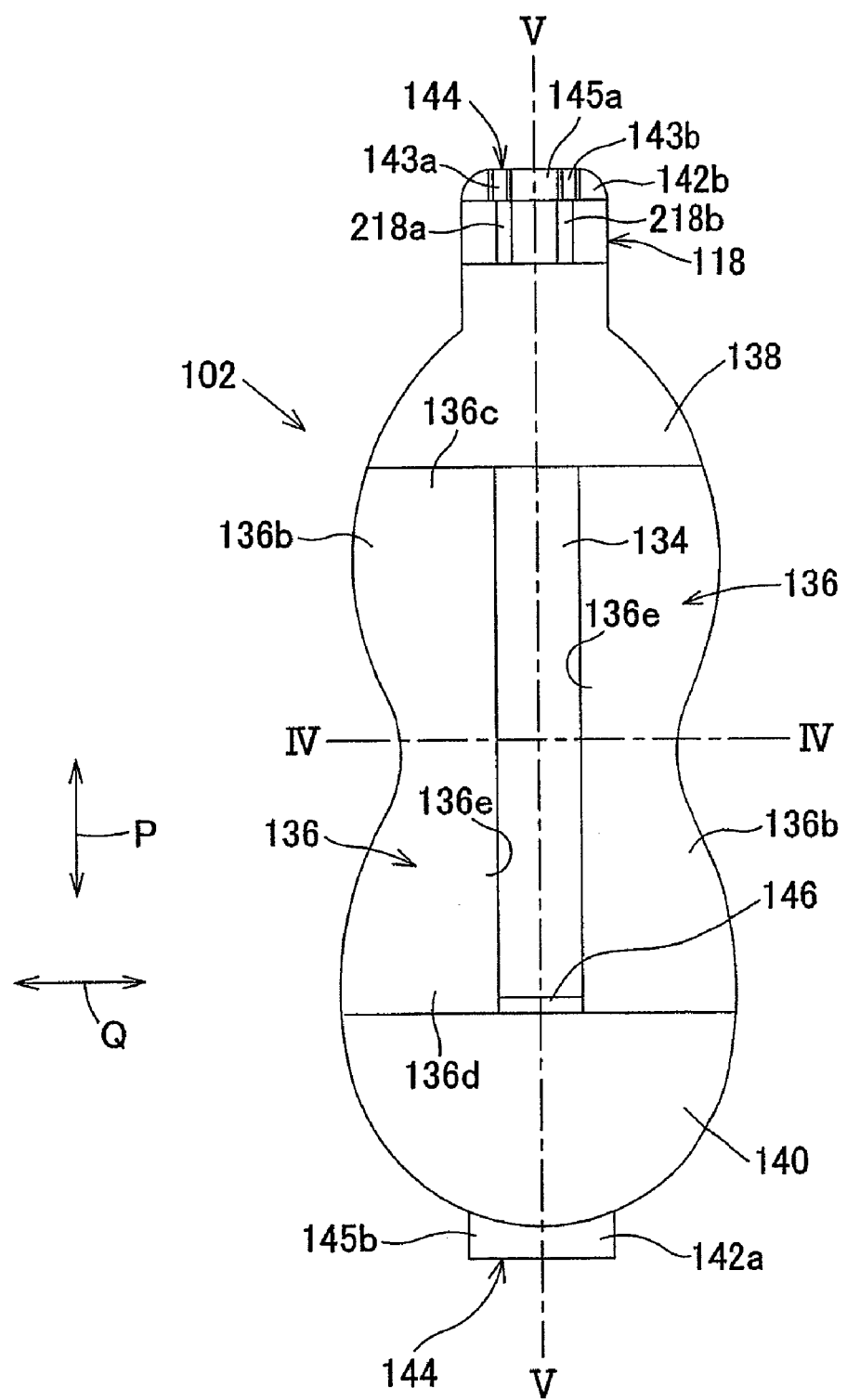
FIG. 3 is a plan view of the urine receiver.
Figure 4:
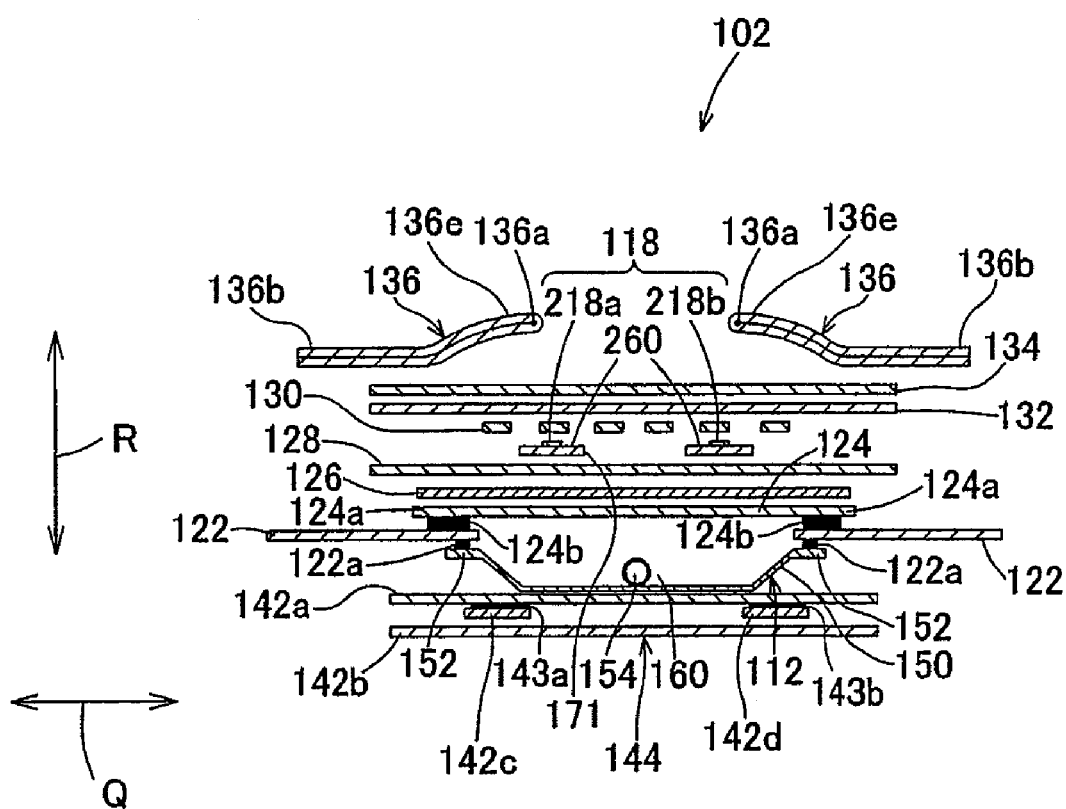
FIG. 4 is a sectional view taken along the line IV-IV in FIG. 3.
Figure 5:
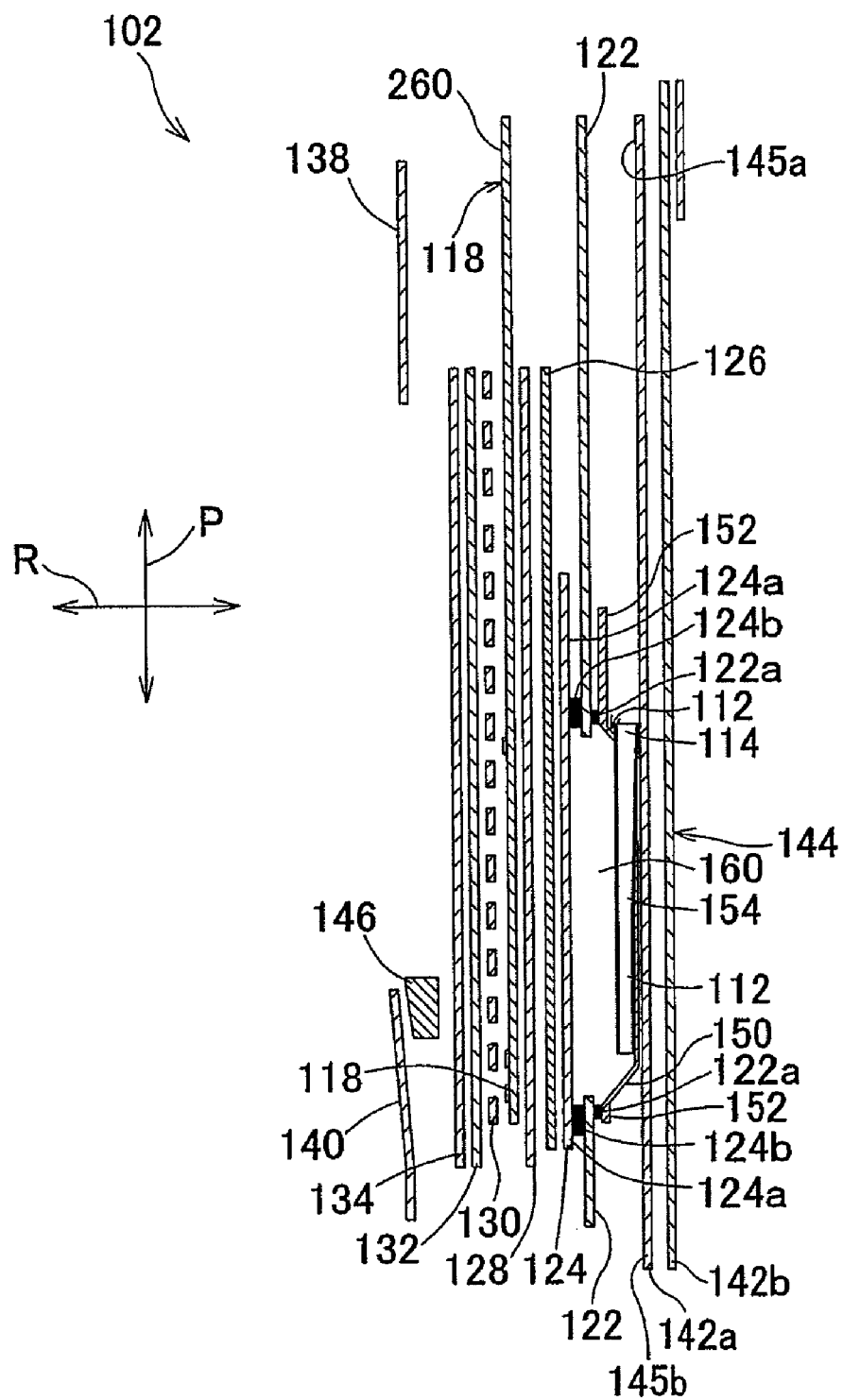
FIG. 5 is a sectional view taken along the line V-V in FIG. 3.

FIG. 3 is a plan view showing the inner side of the urine receiver 102, FIG. 4 is a sectional view taken along the line IV-IV in FIG. 3 and FIG. 5 is a sectional view taken along the line V-V in FIG. 3. In FIGS. 4 and 5, most of the members stacked together in a thickness direction R (see FIG. 4) of the urine receiver 102 are illustrated to be spaced one from another.

Referring to FIGS. 3 and 4, the urine receiver 102 has a length direction P corresponding to the vertical direction of the wearer's body and a width direction Q which is orthogonal to the length direction P. The urine receiver 102 has a width which is relative large in the vicinity of its opposite end sections as viewed in the length direction P and gradually reduced in its middle section. The urine receiver 102 has a thickness direction R also, and comprises the container member 112, a liquid-impervious backsheet 122, a substantially non-breathable liquid-pervious sheet 124, a diffusive sheet 126, a cushion sheet 128, the urine sensor 118, a protective spacer 130 for the urine sensor 118, a protective sheet-like filter 132 for the urine sensor 118, a liquid-pervious skin-contacting sheet 134 and leak-proof barriers 136 stacked in this order from below.

As seen with the urine receiver 102 flattened, both upper and lower ends of the respective leak-proof barriers 136 are covered with first and second end sheets 138, 140 (see FIG. 3).

If the skin-contacting sheet 134 is contaminated with feces discharged from the wearer of the urine receiver 102, it will be no more possible for the urine receiver 102 to absorb urine. In order to deal with this problem, the urine receiver 102 of FIGS. 3 and 4 is provided with a feces sensor 144. Referring to FIG. 4, the feces sensor 144 comprises a pair of electrodes 143a, 143b formed on thermoplastic synthetic resin films 142c, 142d, for example, by an aluminum evaporation technique. The films 142c, 142d are covered with a pair of cover sheets 142a, 142b. The cover sheets 142a, 142b are liquid-pervious so that an aqueous content of feces is permeable therethrough toward the electrodes 143a, 143b. In such a feces sensor 144, the electrodes 143a, 143b extend in the length direction P in parallel to the electrodes 218a, 218b for urine detection. If a lower end section 145b of the feces sensor 144 as viewed in FIGS. 3 and 5 is contaminated with feces, an aqueous content of feces permeates the cover sheet 142a and electrically connects the electrodes 143a, 143b to each other. Thereupon a power source 116a (see FIG. 1) provided in the wiring supplies an alarm unit with current in the form of signal asking for a treatment of feces and an exchange of the urine receiver 102.

The container member 112 is flexible and may be obtained by an injection molding or other appropriate molding methods of soft elastic material such as soft polyethylene or silicon rubber etc. so that the container member 112 may be flexible in the length direction P as well as in the width direction Q. Referring to FIGS. 4 and 5, the container member 112 is formed along its upper edge 112a with a flange 152 and the backsheet 122 covers the flange 152 and, over the entire circumference of the flange 152, a region 122a of the backsheet 122 is attached to the flange 152 by means of sealing or adhesive agent. Detailed construction of the container member 112 will be described later in reference with FIG. 6.

The backsheet 122 serves to restrain leak-out of the urine from the urine receiver 102 and may be formed by soft liquid-impervious sheet such as polyethylene film or the film laminated with a nonwoven fabric. For example, FIG. 4 shows the backsheet 122 formed by polyethylene film having a thickness of 30 μm. Wile the length and the width of the backsheet 122 may be optionally dimensioned, the backsheet 122 exemplarily depicted in FIGS. 4 and 5 is dimensioned so as to substantially correspond to the contour of the urine receiver of FIG. 3.

The highly liquid-pervious but substantially air-impervious sheet 124 covers the opening of the container member 112 and has its peripheral edge 124a of which region 124b is attached to the backsheet 122, more preferably not only to the backsheet 122 but also to the entire circumference of the flange 152 through the backsheet 122 by melt-bonding or adhesive agent. In this manner, the liquid-pervious sheet 124 cooperates with the container member 112 to define a urine suction space 160. The urine suction space 160 has its opening covered by the substantially non-breathable liquid-pervious sheet 124 and therefore a negative pressure can be easily generated within the container member 112 sufficient to suck the urine discharged onto the urine receiver 102. As stock material for this liquid-pervious sheet 124, a nonwoven fabric maybe used. An example of the material is SMS nonwoven fabric consisting of spun-bonded nonwoven fabric with a basis weight of 22 g/m², melt-blown nonwoven fabric with a basis weight of 10 g/m² and spun-bonded nonwoven fabric with a basis weight of 22 g/m², which is preferably modified by a hydrophilic surfactant. A description as used herein, "the liquid-pervious sheet 124 is substantially air-impervious", refers to a fact that the air-permeability value of this sheet 124 obtained by Air-Permeability Measuring Method A specified by JIS L 1096, Section 6.27.1 is in a range of 0 to 100 cc/cm²/sec, more preferably in a range of 0 to 50 cc/cm²/sec in a wet condition and in a range of 20 to 200 cc/cm²/sec, more preferably in a range of 20 to 100 cc/cm²/sec, further more preferably in a range of 20 to 50 cc/cm²/sec in a dry condition. A description as used herein, "wet condition", under which the air-permeability is measured refers to a condition as follows: a weight of the nonwoven fabric kept under the condition of 20° C. and RH 60% for 24 hours at minimum is assumed to be a weight of this sheet under a dried condition, a weight of this nonwoven fabric immersed in water and then suspended for 5 minutes for water drip is assumed to be a weight of this sheet under a wet condition, and "wet condition" refers to the condition that the aqueous content of the nonwoven fabric calculated from the following equation (1) is 100% or higher.

Moisture content (%)=(weight of sheet under wet condition−weight of sheet under dried condition)/ (weight of sheet under dried condition)   equation (1)

The diffusive sheet 126 is formed by a sheet material such as nonwoven fabric or tissue paper containing hydrophilic fiber such as rayon of 40% by weight or higher and having a basis weight in a range of 10 to 30 g/m². Urine discharged from the wearer of the urine receiver 102 quickly spreads on this diffusive sheet 126 which causes, in turn, the liquid-pervious sheet 124 to be wet at once over its wide area. This diffusive sheet 126 is intermittently bonded to the liquid-pervious sheet 124 by means of melt-bonding or adhesive agent. The liquid-pervious sheet 124 which is wet over its wide area causes the urine suction space 160 defined by the container member 112 to rapidly reach a sufficiently high degree of vacuum to suck the urine into the container member 112. The diffusive sheet 126 laminated with the liquid-pervious sheet 124 as shown has the air-permeability as well as the liquid-permeability higher than those of the liquid-pervious sheet 124.

The cushion sheet 128 is formed, for example, by a thermal-bonded nonwoven fabric having a basis weight in a range of 20 to 30 g/m² and has two roles. The one is to pick up urine instantaneously at the initial stage of urination and the other is to serve as a carrier sheet on which some components such as the urine sensor 118, the urine sensor protection spacer 130 in a form of net and the urine sensor protection filter sheet 132 are laid at predetermined positions, respectively.

The urine sensor 118 comprises a flexible thermoplastic synthetic resin film 260 such as polyethylene film and a pair of the electrodes 218a, 218b formed by coating or printing the film 260 with a conductive material. These electrodes 218a, 218b extend in parallel to each other in the length direction P of the urine receiver 102 on both sides of a through-hole 171 of the film 260. Referring to FIG. 3, respective upper ends of these electrodes 218a, 218b extend upward beyond the upper edge of the end sheet 138 so as to be held by the clip 120 (see FIGS. 1 and 2). In this urine sensor 118, the pump unit 108 is applied with a signal indicating a urination as these electrodes 218a, 218b are electrically connected to each other via urine. The urine sensor 118 is provided on the upper side of the liquid-pervious sheet 124 as viewed in the thickness direction R. If the urine sensor 118 has neither the diffusive sheet 126 nor the cushion sheet 128, the urine sensor 118 is attached directly to the liquid-pervious sheet 124. However, it is preferred to attach the urine sensor 118 to the cushion sheet 128 by melt-bonding or adhesive agent so that the paired electrodes 218a, 218b may be spaced from each other by a constant distance in the width direction Q. Between the electrodes 218a, 218b spaced from each other in the width direction Q, the cushion sheet 128 is exposed in the through-hole 171 of the film 260.

Referring to FIG. 4, the urine sensor 118 is protectively covered from the above with the spacer 130 formed by a thermoplastic synthetic resin mesh sheet and having a thickness of at least 0.7 mm and the filter sheet 132 formed by, for example, a spun-bonded nonwoven fabric having a basis weight in a range of 15 to 25 g/m². The spacer 130 and the filter sheet 132 may be attached to each other by melt-bonding or adhesive agent and both of these sheets 130, 132 may be attached to the cushion sheet 128 by means of melt-bonding or adhesive agent. The spacer 130 is used to space the filter 132 and the sensor 118 from each other in the thickness direction R and thereby to eliminate a possibility that the wet filter 132 might continue to be in contact with the sensor 118 particularly when the urine receiver 102 is loaded with the wearer' body weight. The spacer 130 is made of a mesh sheet having air-permeability as well as liquid-permeability higher those of the liquid-pervious sheet 124 and ensuring that its thickness is kept constant in a substantial meaning. In order to get a smooth permeation of urine, the mesh sheet has preferably through holes whose diameters are at least 2 mm. The filter 132 is useful to prevent a case that solid content of bodily discharges might cling to the sensor 118 to make the sensor 118 permanently conductive and cause a malfunction. The filter 132 preferably has air- and liquid-permeabilities higher than those of the liquid-pervious sheet 124.

The skin-contacting sheet 134 laid above the filter 132 is formed by a soft and liquid-pervious sheet such as a thermal bonded nonwoven fabric having a basis weight in a range of 15 to 25 g/m². The skin-contacting sheet 134 faces the wearer' urethral and skin therearound and may be hydrophilic or water-repellent so far as this sheet 134 does not affect quick transfer of urine into the urine receiver 102. The skin-contacting sheet 134 has air- and liquid-permeabilities higher those of the liquid-pervious sheet 124 and is preferably attached to the filter 132 by melt-bonding or adhesive agent.

A pair of the leak-proof barriers 136 shown by FIG. 4 serves to prevent the urine from moving on the skin-contacting sheet 134 in the width direction Q beyond the urine receiver and leaking sideways. Each of the leak-proof barriers 136 is attached to the skin-contacting sheet 134 along an outer side edge 136b located in the vicinity of the associated outer side edge of the urine receiver 102 as viewed in the width direction Q and at opposite ends 136c, 136d (see FIG. 3) located in the vicinity of the opposite ends of the urine receiver 102 as viewed in the length direction P. The inner side edge 136e of the leak-proof barrier 136 located immediately inside the line V-V in FIG. 3 corresponding to the center line bisecting the width of the urine receiver 102 is left free from the skin-contacting sheet 134. The inner side edge 136e is provided with an elastic member 136a stretched in the length direction P and bonded in this stretched state to the inner side edge 136e. The inner side edge 136e of the leak-proof barrier 136 rises off above the skin-contacting sheet 134 as the urine receiver 102 is curved along the wearer's skin in the length direction P and the elastic member 136a contracts. Since the leak-proof barrier 136 is a region to be directly in contact with the wearer's skin, a stock material for the barrier 136 is preferably selected from a group including soft thermoplastic synthetic resin film or the film laminated with a nonwoven fabric and the stock material is preferably liquid-impervious. In the vicinity of the opposite ends 136c, 136d, the leak-proof barrier 136 are covered with the end sheets 138, 140, respectively (see FIGS. 3 and 5).

Referring to FIGS. 3 and 5, between the paired leak-proof barriers 136 in the vicinity of the lower end sheet 140, there is provided a soft and elastic fibrous bulky agglomerate 146 formed, for example, by a thermal-bonded nonwoven fabric as a means to fill the wearer's bottom cleavage. This fibrous agglomerate 146 functions to guide the urine which may flow backwardly along the bottom cleavage of the wearer toward the container member 112. The position at which such a fibrous agglomerate 146 is provided is preferably selected depending on whether the urine receiver 102 is for men or for women. For example, in the case of the urine receiver 102 for women, the fibrous agglomerate 146 is preferably provided in the vicinity of the end sheet 140 as shown in FIGS. 3 and 5, while, in the case of the urine receiver 102 for men, the fibrous agglomerate 146 is preferably provided aside toward above with respect to the case of the urine receiver 102 for women.

The urine receiver 102 includes the feces sensor 144 comprising, below the container member 112 as viewed in the thickness direction R, two cover sheets 142a, 142b and a pair of electrodes 143a, 143b covered with these cover sheets 142a, 142b, respectively. The electrodes 143a, 143b are formed by aluminum evaporation technique on a thermoplastic synthetic resin film. As a stock material for the cover sheets 142a, 142b, for example, liquid-pervious spun-bonded nonwoven fabric having a basis weight in a range of 15 to 21 g/m$^2$. As viewed in the length direction P in FIG. 5, the feces sensor 144 has an end 145b extending downward from the end sheet 140 and an end 145a extending upward from the end sheet 138 beyond the urine sensor 118. With the urine sensor 102 put on the wearer's body, the end 145b of the feces sensor 144 is placed aside the anus. If feces is discharged, it clings to the end 145b and then permeates any one of the cover sheets 142a, 142b resulting in an electrical connection of the paired electrodes 143a, 143b, the feces sensor 144 is activated to output a signal indicating a defecation to a display (not shown) provided on the pump unit 108. The electrodes 143a, 143b exposed at the end 145a are held by the clip 120 and electrically connected to the wiring 116. The cover sheets 142a, 142b may be formed by a hydrophobic nonwoven fabric to avoid a case that the paired electrodes 143a, 143b might be electrically connected to each other due to sweat of the wearer and the feces sensor 144 might erroneously output a signal indicative of defecation. The cover sheets 142a, 142b are attached to the container member 112 and the backsheet 122 by means of melt-bonding or adhesive agent.

The urine receiver 102 will lose its capability to suck urine, if the skin-contacting sheet 134 is contaminated with feces. Therefore, if the feces sensor 144 detects the feces, the urine receiver 102 is preferably exchanged with a fresh one as rapidly as possible.

Figure 6:
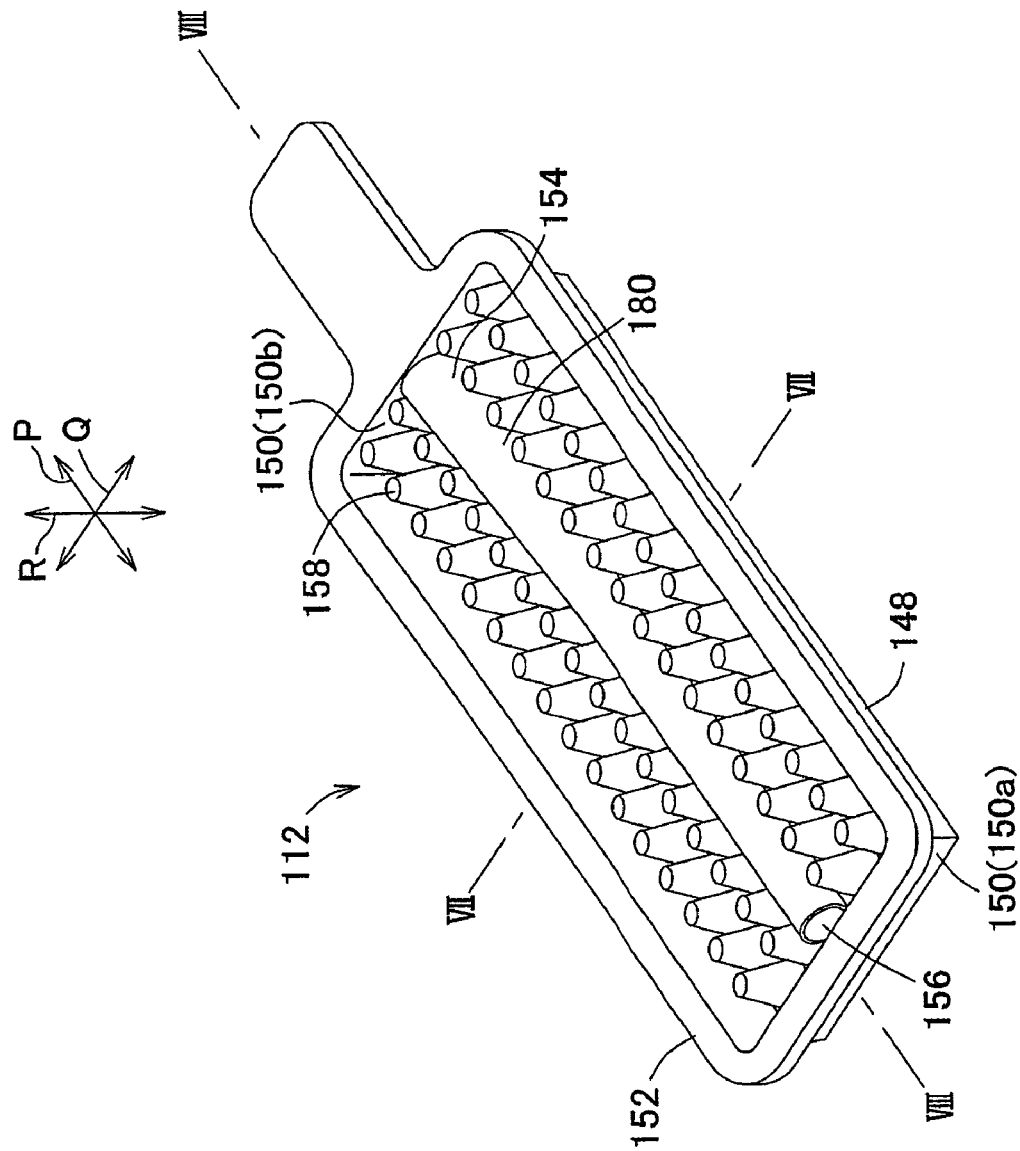
FIG. 6 is a perspective view of a container member.
Figure 7:
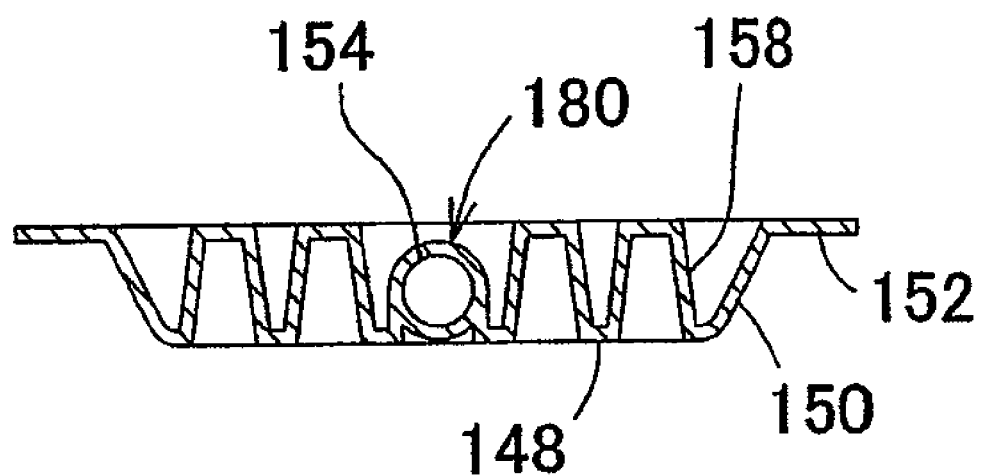
FIG. 7 is a sectional view taken along the line VII-VII in FIG. 6.
Figure 8:
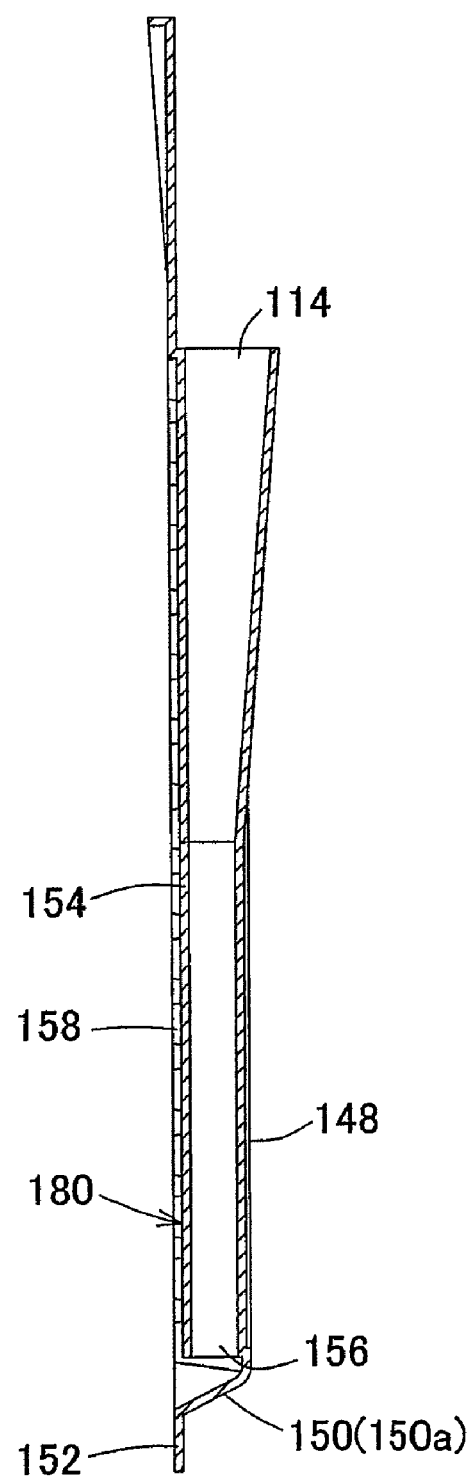
FIG. 8 is a sectional view taken along the line VIII-VIII in FIG. 6.
Figure 9:
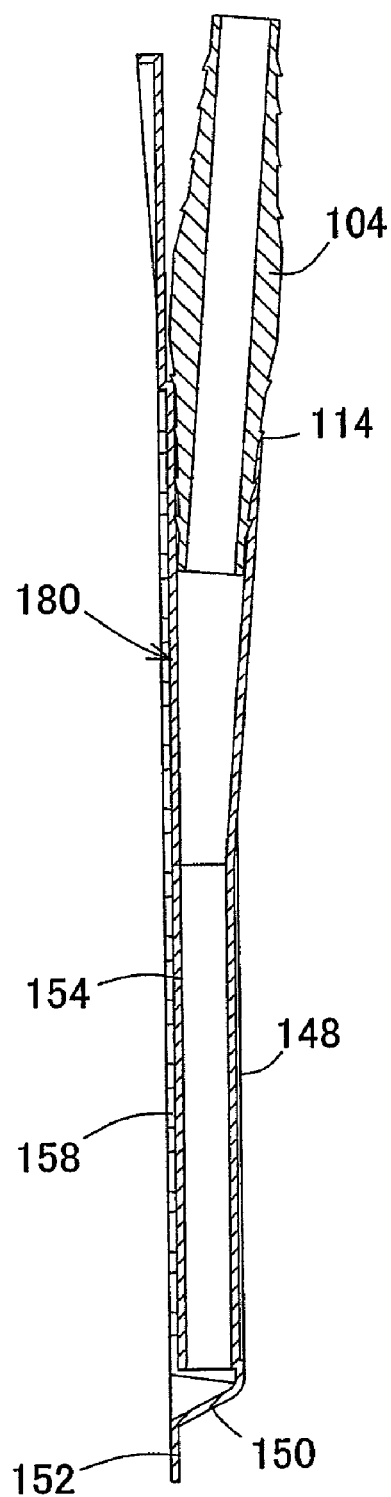
FIG. 9 is a view similar to FIG. 8, showing the container member together with a joint member inserted thereinto.

FIG. 6 is a perspective view showing the container member 112 included in the urine receiver 102, FIG. 7 is a sectional view taken along the line VII-VII in FIG. 6, FIG. 8 is a sectional view taken along the line VIII-VIII in FIG. 6 and FIG. 9 is a view similar to FIG. 8, showing the container member 112 provided with the joint member 104.

Referring to FIGS. 6 through 9, the container member 112 is a hollow structure having the length direction P, the width direction Q and the thickness direction R which are orthogonal one to another and comprises a bottom 148, a peripheral wall 150 extending up- and outward from the periphery of the bottom 148 substantially in the thickness direction R, and the flange 152 horizontally extending outward from the top edge of the peripheral wall 150. The backsheet 122 is water-tightly and permanently attached to the inner surface (i.e., upper surface as viewed in FIG. 7) of the flange 152 (see FIG. 4). Owing to the upper flat surface of the flange 152 the backsheet 122 is easily attached to the container member 112 and also the backsheet 122 is water-tightly attached to the container member 112, and, thereby, it is possible to prevent a leakage of urine from between the backsheet 122 and the flange 152.

As will be apparent from FIG. 6, the container member 112 is provided with a suction part 180 adapted to collect the amount of urine flowing into the container member 112 and then to evacuate this from the container member 112. The suction part 180 comprises a urine guide suction tube 154 provided on a substantially middle zone of the container member 112 as viewed in the width direction Q so as to extend in the length direction P, a urine suction port 156 opening toward the interior of the container member 112 at the inner end of the suction tube 154, i.e., at the left end as viewed in FIG. 6, and a urine evacuation port 114 opening toward the exterior of the container member 112 at the right end as viewed in FIG. 6. The preferred urine suction port 156 is formed so as to be spaced by 2 to 7 mm from the inner surface of the peripheral wall 150a of the two peripheral walls 150a, 150b opposed to each other in the length direction P of the container member 112, which takes a lower position when the urine receiver 102 is put on the wearer. For example, with the suction tube 154 having its inner diameter in a range of 4 to 6 mm, the urine suction port 156 is preferably spaced from the peripheral wall 150a by the order of 3 mm. With the urine suction port 156 positioned near to the peripheral wall 150a, even if the container member 112 is curved and consequently the liquid-pervious sheet 124 trails down onto the inner side of the container member 112 during use of the urine receiver as shown by FIG. 2, it is possible to prevent a case that the liquid-pervious sheet 124 might trail down into the narrow gap between the urine suction port 156 and the peripheral wall 150a and might block off the urine suction port 156. The suction tube 154 extends from the vicinity of the one peripheral wall 150a toward the opposite peripheral wall 150b with its inner diameter gradually enlarged from the urine suction port 156 to the urine evacuation port 114. As shown by FIG. 8, the urine evacuation port 114 is formed on the lower side of the flange 152, preferably so as to be spaced from the flange 152 at least by 3 mm. The urine evacuation port 114 arranged in this manner facilitates the joint member 104 to be inserted and, in addition, prevent a case that an insertion of the joint member 104 might cause the inner surface of the flange 152 to be distorted.

Within the container member 112, a plurality of substantially circular truncated cone-shaped protuberances 158 are provided at regular intervals in straight lines in a length direction P as well as in the width direction Q so that a space between the liquid-pervious sheet 124 and the bottom 148 of the container member 112, i.e., the urine suction space 160 (see FIGS. 7 and 10) defined by the container member 112 and the liquid-pervious sheet 124 can be maintained by preventing the liquid-pervious sheet 124 from sagging and/or bending when urine is sucked by the suction pump. When the urine receiver 102 is kept in contact with the skin, the container member 112 is smoothly bowed in the length direction P as well as in the width direction Q along the lines defined between the protuberances 158.

Figure 10:
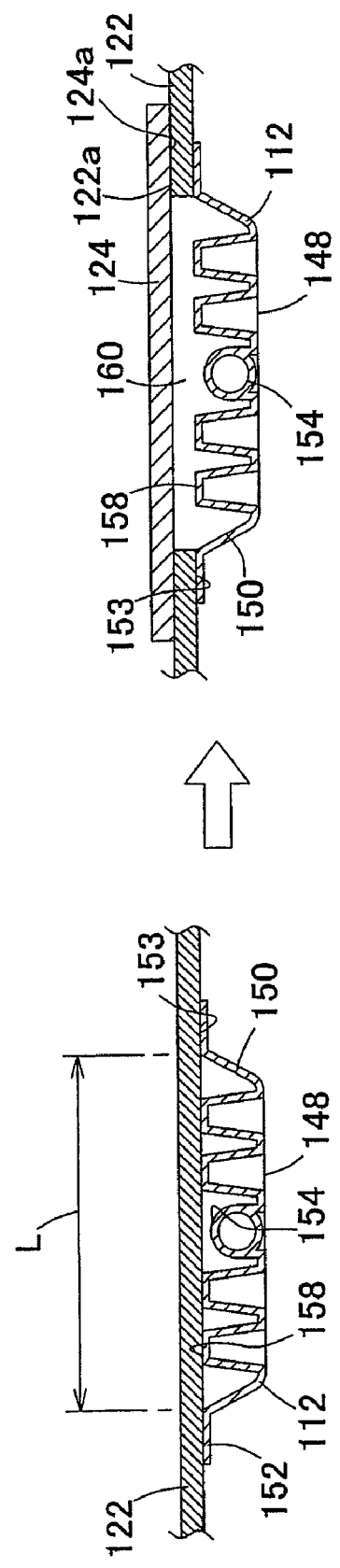
FIG. 10 is a diagram illustrating a step in which a backsheet and a liquid-pervious sheet are attached to the joint member.

FIG. 10 is a diagram exemplarily illustrating a process in which the backsheet 122 and the liquid-pervious sheet 124 are attached to the container member 112. A sheet material to be used as the backsheet 122 is placed against and attached to the flange 152 of the container member 112 by melt-bonding, ultra sonic sealing or adhesive agent such as hot melt adhesive agent. Then, a portion L of this sheet material extending inside the flange 152 is cut off and the liquid-pervious sheet 124 is placed upon the inner surface (i.e., the upper surface as viewed in FIG. 10). The liquid-pervious sheet 124 is attached to the backsheet 122 or to the backsheet 122 and the flange 152.

In the container member 112 cooperating with the liquid-pervious sheet 124 to form the urine suction space 160, when a negative pressure is generated within the urine reservoir 106a by activating the suction pump of the pump unit 108 after the urine guide tube 106 has been connected to the urine evacuation port 114 of the suction tube 154, a negative pressure is succeedingly generated within the urine suction space 160 via the urine guide tube 106, the joint member 104 and the suction tube 154. In this way, the urine still present outside the container member 112 can be guided into the container member 112 via the liquid-pervious sheet 124, then the urine can be collected in the vicinity of the peripheral wall 150a (see FIG. 8) of the container member 112 and finally transferred through the urine suction port 156 into the urine reservoir 106a.

Figure 11:
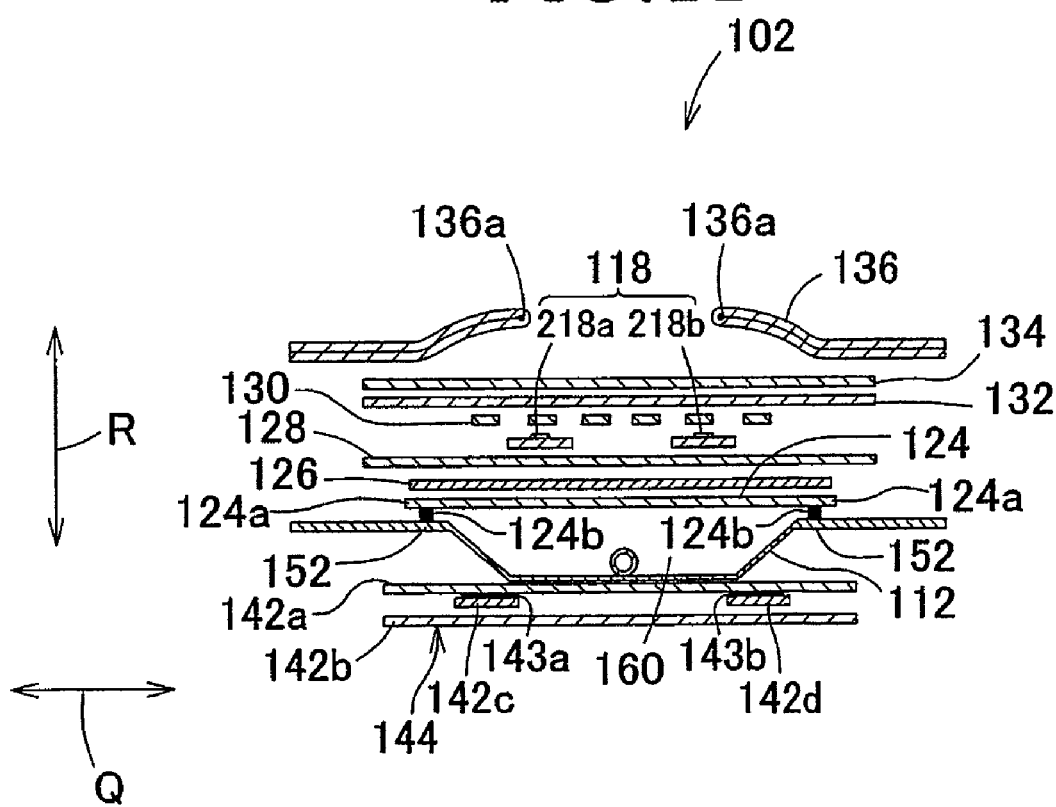
FIG. 11 is a view similar to FIG. 4, showing an embodiment of the invention.
Figure 12:
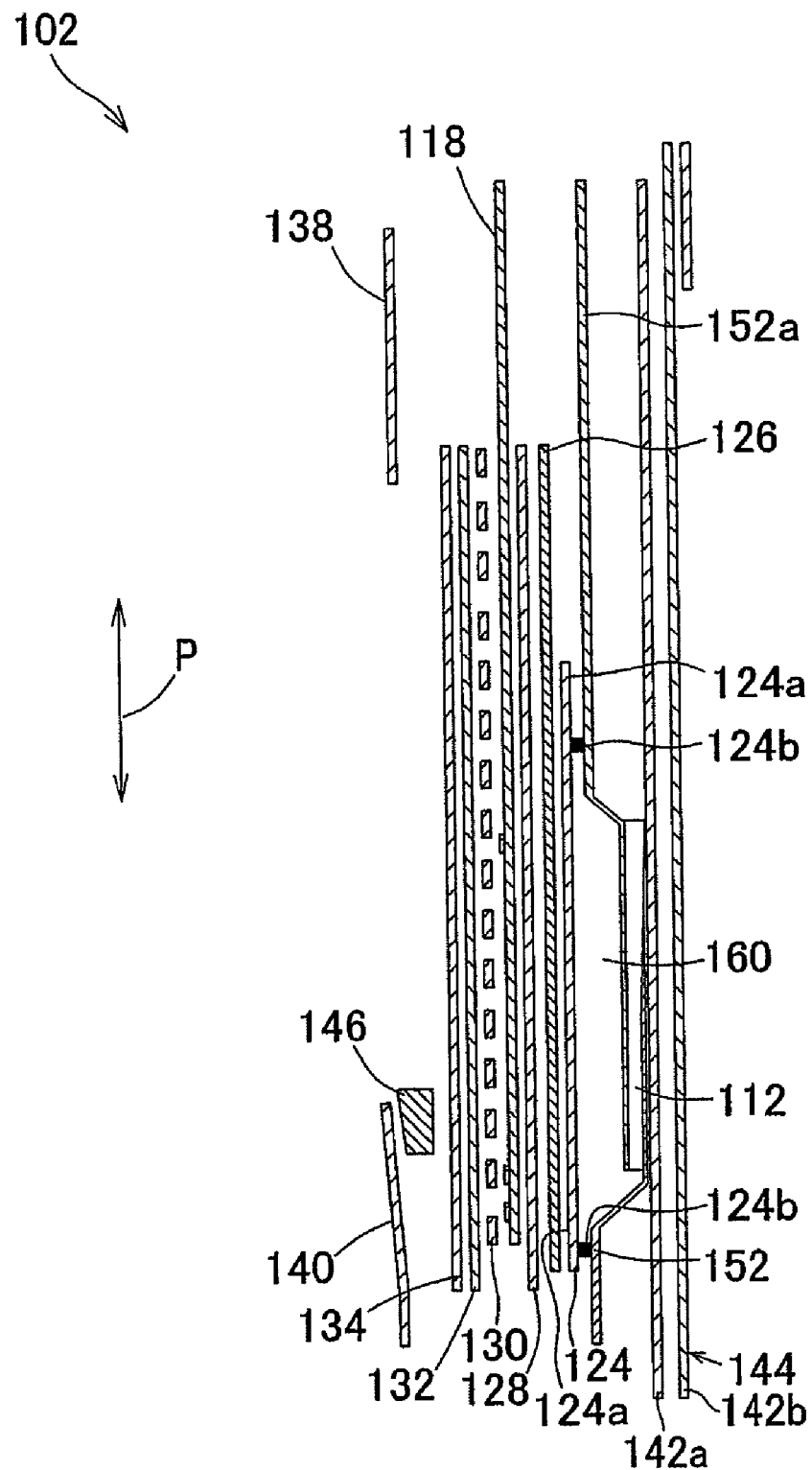
FIG. 12 is a view similar to FIG. 5, showing an embodiment of the invention.

FIGS. 11 and 12 are views similar to FIGS. 4 and 5, respectively, showing one preferred embodiment of the present invention. The urine receiver 102 of FIGS. 11 and 12 is distinguished from that of FIGS. 4 and 5 in that no backsheet 122 is used and the peripheral edge 124a of the liquid-pervious sheet 124 is permanently attached in its region 124b to the entire circumference of the flange 152 of the container member 112. If it is desired to reduce the length and the width of the urine receiver 102, the urine receiver 102 may be made without the backsheet 122 as in the case of the embodiment shown. Preferably for the urine receiver 102 according to this embodiment, the leak-proof barriers 136 as well as the end sheets 138, 140 are formed using a liquid-impervious sheet and water-tightly attached to the flange 152 of the container member 112 and thereby the urine collected within the container member 112 is prevented from leaking out along the flange 152. The dimension of the flange 152 is optional in the vertical direction P as well as in the width direction Q so far as the wearer accepts the feeling to wear the urine receiver 102.

While it is preferred to cover the urine sensor 118 with the skin-contacting sheet 134, the filter 132, the spacer 130 and the others in order to get good features of the urine sensor 118 in accordance with the present invention, it is possible to implement the invention, if any of the spacer 130, the filter 132, the skin-contacting sheet 134, the leak-proof barriers 136 and the feces sensor 144 is omitted from the urine receiver 102 of FIGS. 11 and 12. In the embodiment shown by FIG. 5 wherein the backsheet 122 is used, the backsheet 122 may be water-tightly fixed to the flange 152, the liquid-pervious sheet 124 may be attached to the inner surface of this backsheet 122 and thereby the liquid-pervious sheet 124 is indirectly attached to the flange 152 to ensure that the urine contained by the liquid-pervious sheet 124 can be easily prevented against exuding out from the urine receiver 102. However, it should be noted that the present invention does not exclude the construction in which the liquid-pervious sheet 124 is fixed directly to the flange 152 as will be obvious from FIGS. 11 and 12.

Figure 13:
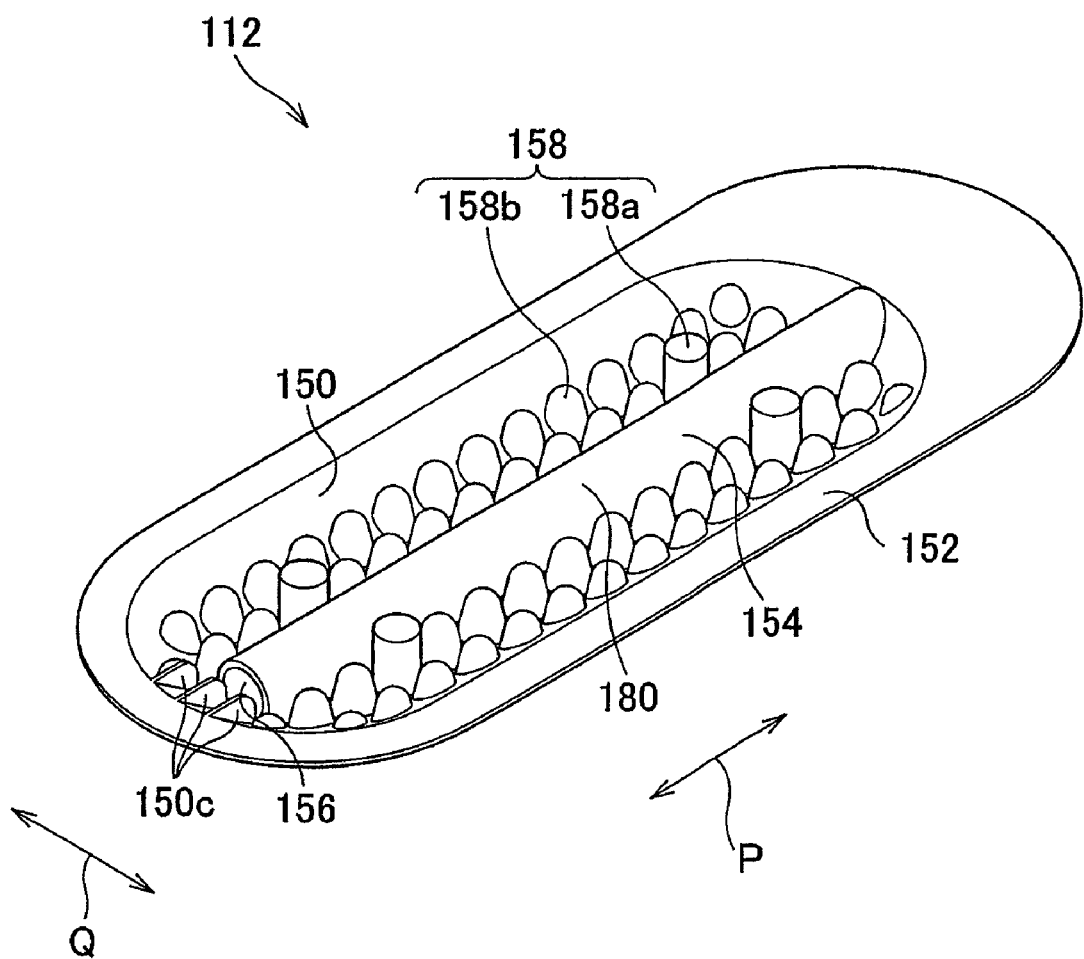
FIG. 13 is a perspective view showing a container member different from that of FIG. 6.

FIG. 13 is a perspective view showing the container member 112 according to an embodiment differing from the embodiment of FIG. 6 and this container member 112 of FIG. 13 is also adapted to be used in combination with the urine receiver 102 according to the present invention. This container member 112 has an oval shape and the peripheral wall 150 is formed with three ribs 150c. The suction tube 154 provided on a substantially middle zone of the container member 112 as viewed in the width direction Q so as to extend in the length direction P, a urine suction port 156 is opposed to the rib 150 and spaced from the rib 150 by 2 to 7 mm. The bottom 151 (see FIG. 14) of the container member 112 is formed with a plurality of protuberances 158 including first protuberances 158a as high as substantially reaching the level as the flange 152 and second protuberances 158b which are lower than the first protuberances 158a.

Figure 14:
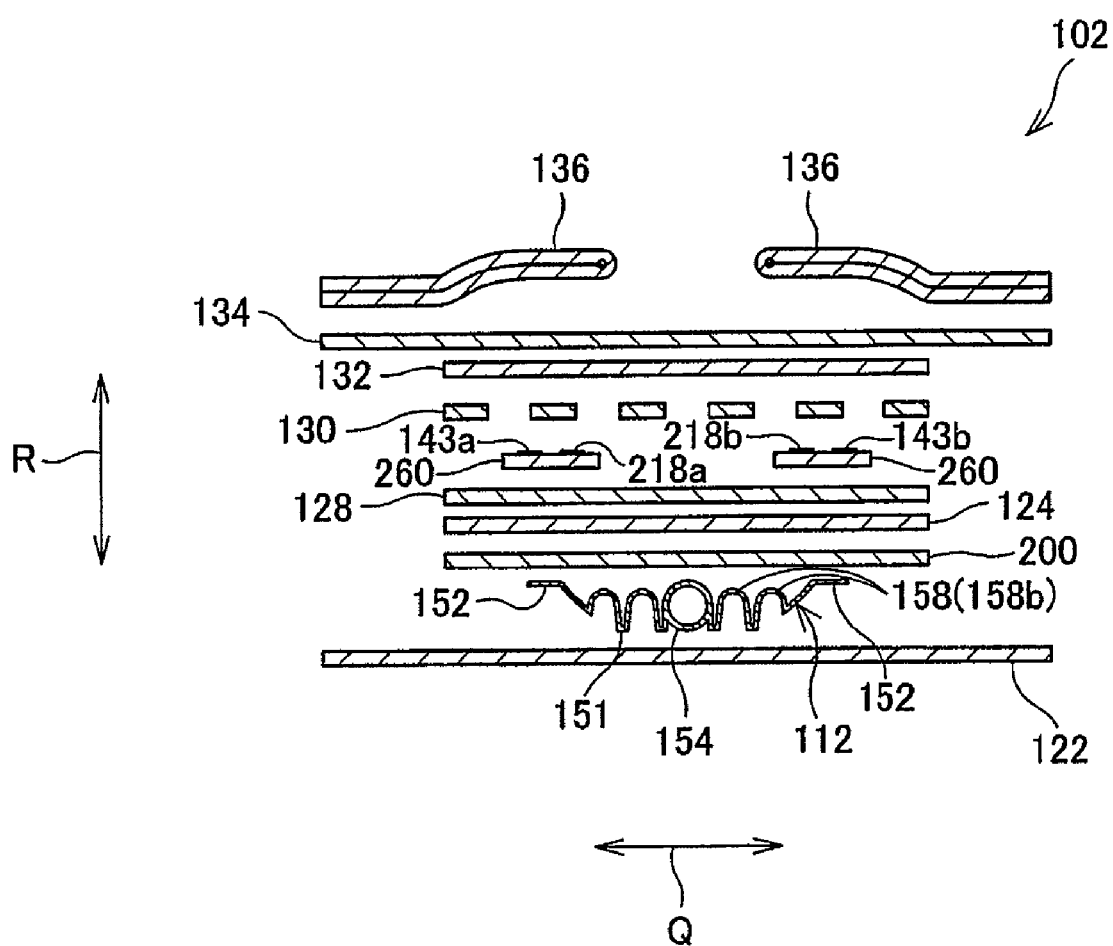
FIG. 14 is a view similar to FIG. 4, showing an embodiment of the urine receiver.
Figure 15:
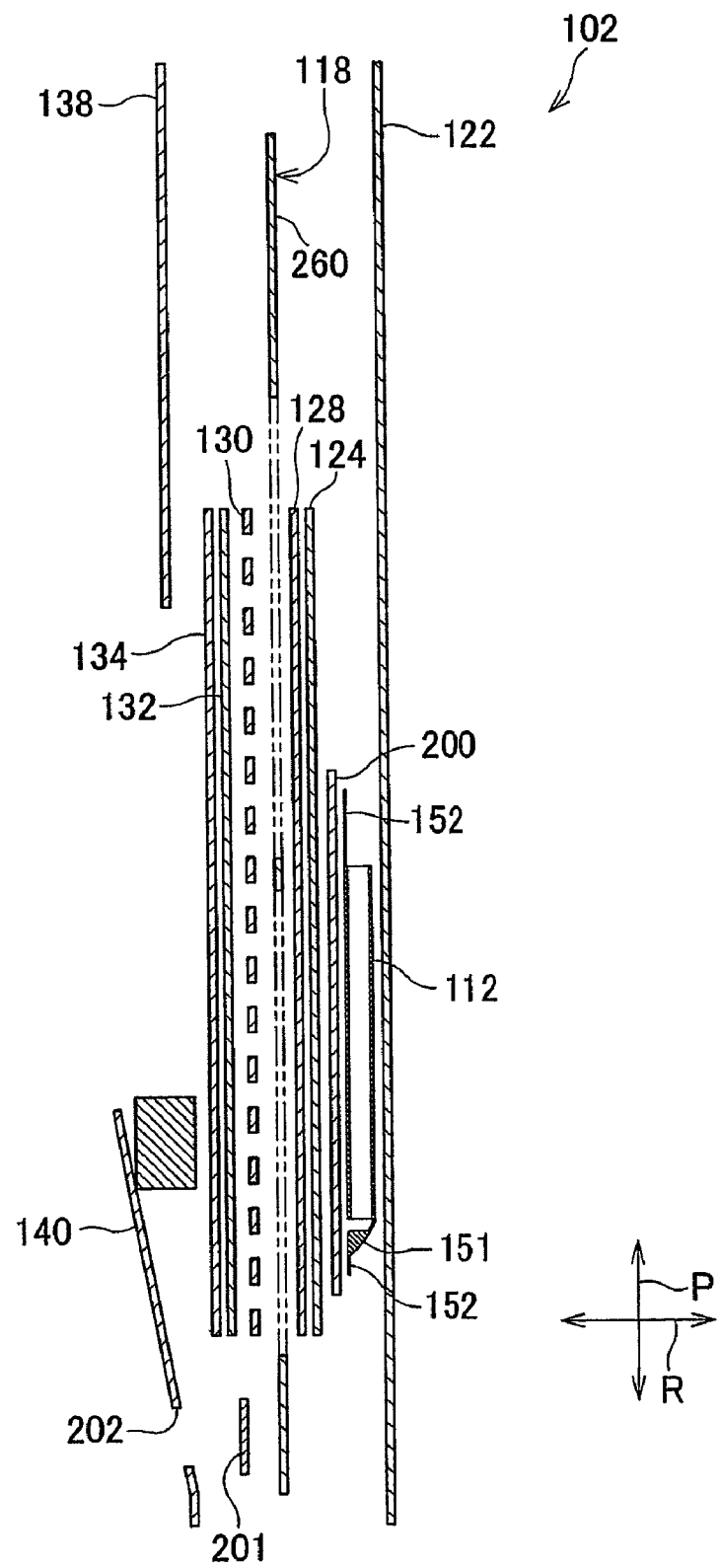
FIG. 15 is a view similar to FIG. 4, showing another embodiment of the urine receiver.

FIGS. 14 and 15 are views similar to FIGS. 4 and 5, respectively, showing an embodiment of the urine receiver 102 using the container member 112 of FIG. 13. In FIGS. 14 and 15, the respective members stacked one upon another in the thickness direction R is illustrated to be spaced one from another. This urine receiver 102 is provided on its outer side with the liquid-impervious backsheet 122 extending outward from the periphery of the container member 112 in the length direction P as well as in the width direction Q. The container member 112 is provided on its inner side with a bond sheet 200, the substantially air-impermeable liquid-pervious sheet 124, the cushion sheet 128, the urine sensor 118, the spacer 130, the filter 132, the skin-contacting sheet 134 and the leak-proof barriers 136 placed one upon another as illustrated.

The bond sheet 200 is used to facilitate the liquid-pervious sheet 124 to be attached to the flange 152 of the container member 112. For example, if the container member 112 is made of polyethylene and the liquid-pervious sheet 124 is made of such a material as rayon fiber, polypropylene fiber or polyester fiber who has a melting temperature higher than that of polyethylene of the container member 112, resin containing material having a melting temperature substantially same as or lower than that of the resin forming the container member 112 may be used as the bond sheet 200. For example, the bond sheet 200 may be a spun-bonded nonwoven fabric formed by polyethylene/polypropylene composite fiber of side-by-side type. The liquid-pervious sheet 124 can be easily attached to the flange 152 over its entire circumference by meeting polyethylene contained in the composite fiber interposed between the liquid-pervious sheet 124 and the flange 152 under compression in the thickness direction R. Such a bond sheet 200 may be used so as to cover both of the flange 152 and the upper opening or so as to cover the flange 152 alone.

The liquid-pervious sheet 124 of FIGS. 14 and 15 has at the same time the function of the liquid-pervious sheet 124 and the function of the diffusive sheet 126 of FIGS. 4 and 5. This liquid-pervious sheet 124 of FIGS. 14 and 15 is formed by a spun lace nonwoven fabric containing rayon fiber at a rate of 40% by weight or more with a fineness in a range of 1 to 6 dtex and a length in a range of 20 to 60 mm. The liquid-pervious sheet 124 may also contain thermoplastic synthetic fiber at a rate of 60% by weight or less with a fineness in a range of 1 to 6 dtex and a length in a range of 20 to 60 mm. Similarly to the liquid-pervious sheet 124 of FIG. 4, the liquid-pervious sheet 124 of FIGS. 14 and 15 has air-permeability in a range of 0 to 100 $cc/cm^2/sec$ in the wet condition and a range of 20 to 200 $cc/cm^2/sec$ in the dried condition. The liquid-pervious sheet 124 containing rayon fiber at a rate of 40% by weight or more can diffuse urine as quickly as the diffusive sheet 126 of FIG. 4 can diffuse urine. While the specified air-permeability is preferably met by the liquid-pervious sheet 124 itself, the specified air-permeability may be met by the liquid-pervious sheet 124 placed upon and at least partially attached to the bond sheet 200 entirely covering the opening of the container member 112 as shown by FIGS. 14 and 15.

The cushion sheet 128 may be formed by the same material as that of the cushion sheet 128 of FIGS. 4 and 5 and have the same size as that of the liquid-pervious sheet 124.

The urine sensor 118 includes the electrodes 218a, 218b for urine detection (see FIG. 16) formed by coating the inner surface of the film 260 with a conductive material. The film 260 extends in the length direction P substantially to the both ends of the backsheet 122. The film 260 is formed on its inner surface with the feces detection electrodes 143a, 143b (see FIG. 16) also.

The spacer 130 may be formed by the same material as that for the spacer 130 of FIGS. 4 and 5 and have the same size as that of the liquid-pervious sheet 124. The spacer 130 extends in the length direction P but does not extend downward as far as the spacer 130 might cover the feces detecting elements 144d, 144e (see FIG. 16) in the feces detection electrodes 143a, 143b.

The filter 132 and the skin-contacting sheet 134 may be formed by the same materials as those for the filter 132 and the skin-contacting sheet 134 of FIGS. 4 and 5, respectively. The filter 132 may have the same size as the liquid-pervious sheet 124. The skin-contacting sheet 134 has the same dimension as that of the liquid-pervious sheet 124 in the length direction P but larger than the liquid-pervious sheet 124 and substantially the same dimension as that of the backsheet 112 in the width direction Q.

As shown by FIG. 15, the ends of the urine receiver 102 opposed to each other in the length direction P are respectively provided with the end sheets 138, 140. These end sheets 138, 140 respectively cover the ends (not shown) of the leak-proof barriers 136 opposed to each other in the length direction P in the same manner as in FIG. 3. Referring to FIGS. 14 and 15, the liquid-pervious sheet 124, the cushion sheet 128, the urine sensor 118, the spacer 130, the filter 132 and the skin-contacting sheet 134 stacked one upon another are bonded one to another in the same manner as in FIGS. 4 and 5. The backsheet 122 is attached not only to the outer surface of the bottom of the container member 112, for example, by means of pressure-sensitive adhesive agent but also at a portion of the back sheet 122 extending outward from the flange 152 of the container member 112 to the skin-contacting sheet 134 and the other sheets from below. The leak-proof barriers 136 are attached to the skin-contacting sheet 134 and the portion of the backsheet 122 extending outward from the periphery of the skin-contacting sheet 134.

Referring to FIG. 15, the feces detecting elements 144d, 144e of the feces detection electrodes 143a, 143b are covered with a nonwoven fabric cover sheet 201 allowing the aqueous content in feces to permeate therethrough. The end sheet 140 lying above the cover sheet 201 is formed with a through-hole 202 so that the end sheet 140 may not cover the detecting element 144d, 144e. The through-hole 202 is to be located in the vicinity of the anus of the wearer of the urine receiver 102.

Figure 16:
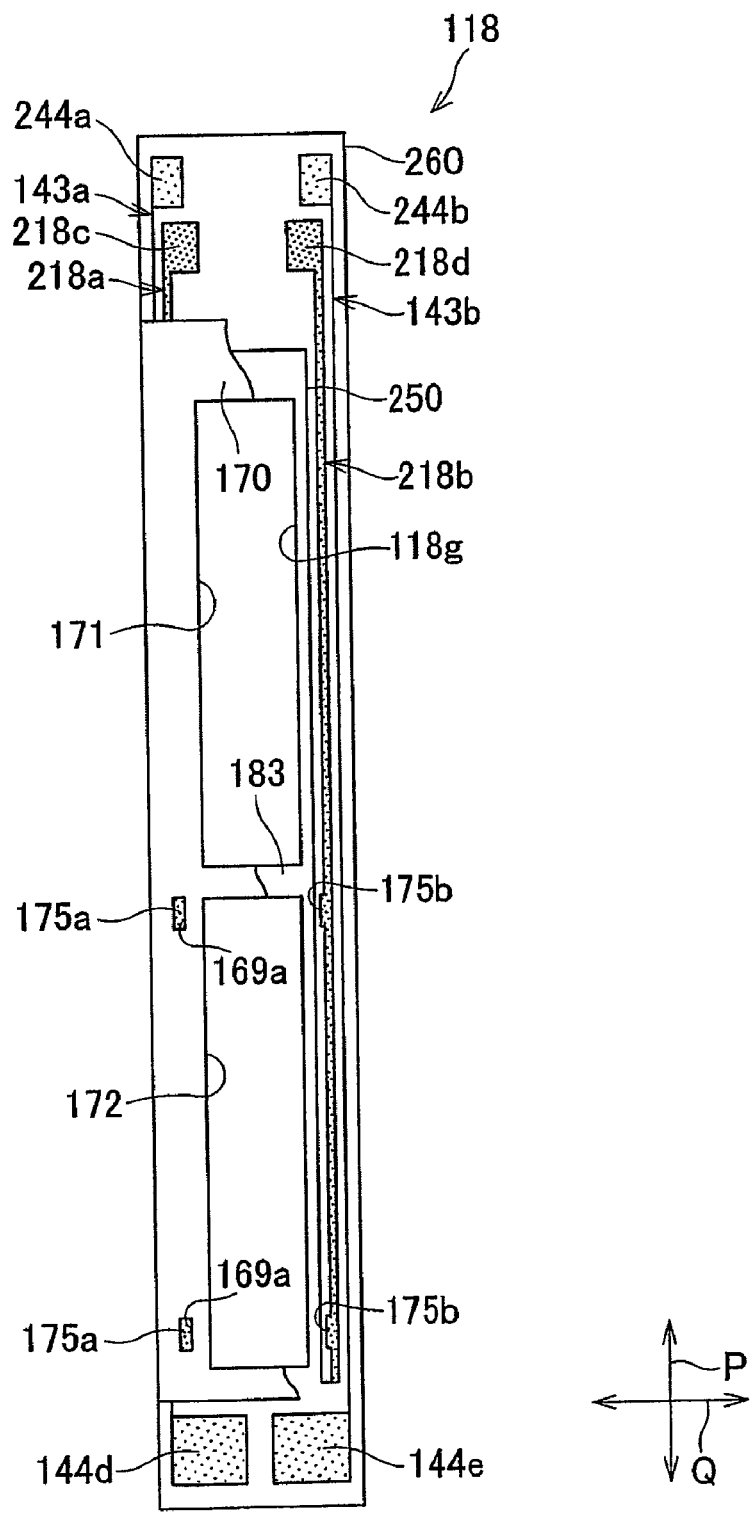
FIG. 16 is a plan view of a urine sensor.

FIG. 16 is a partially broken plan view showing the urine sensor 118 used in the urine receiver 102 of FIGS. 13 and 14. The urine sensor 118 comprises a pair of urine detection electrodes 218a, 218b formed on the inner surface of the liquid-impervious thermoplastic synthetic resin film 260, a pair of feces detection electrodes 143a, 143b and a wiring breakage detection circuit 250. Most part of the electrodes 218a, 218b, 143a, 143b and the entire wiring breakage detection circuit 250 are covered with the insulating coating 170 which is partially shown in FIG. 16. The film 260 is formed in a middle region as viewed in the width direction Q with two through-holes 171, 172 aligned with each other in the length direction P. A bridge 183 is formed between these through-holes 171, 172. The pair of electrodes 218a, 218b as well as the pair of 143a, 143b are formed so as to be opposed to each other about the through-holes 171, 172, respectively, and the wiring breakage detection circuit 250 extends so as to connect each end of the paired urine detection electrodes 218a, 218b. Referring to FIG. 16, the urine detection electrode 218a, 218b has the urine detecting elements 175a exposed in small holes 169a provided in the coating 170 and the urine detection electrode 218b has the urine detecting elements 175b to be exposed in small holes (not shown) to be provided in the coating 170. The feces detection electrodes 143a, 143b include feces detecting elements 144d, 144e provided in the vicinity of the lower end of the urine sensor 118 so that these elements 144d, 144e might not be covered with the coating 170. The urine detection electrodes 218a 218b have connector members 218c, 218d at the upper ends thereof, respectively, and the feces detection electrodes 143a, 143b have connector members 244a, 244b at the upper ends thereof, respectively. The connector members 218c 218d and 244a, 244b are to be held by the clip 120 of FIG. 2. When the urine detecting elements 175a, 175b are electrically connected with each other via urine between the paired urine detection electrodes 218a, 218b, the pump unit 108 is activated. When the feces detecting elements 144d, 144e are electrically connected with each other via aqueous content in feces between the paired feces detection electrodes 143a, 143b, the defecation is signaled as in the case of the urine receiver 102 of FIGS. 4 and 5.

It should be noted that weak current normally flows in the wiring breakage detection circuit 250 so that a wiring breakage alarm device (not shown) included in the pump unit 108 is activated, for example, upon breakage of the urine detection electrodes 218b due to damage and indicates such breakage so as to set off exchange of the urine receiver 102.

According to the present invention the urine receiver which can efficiently and quickly suck urine is manufactured.

What is claimed is:

1. A negative pressure urine receiver adapted to be worn by a wearer in use, said negative pressure urine receiver comprising:
    a leak-proof container member having an opening;
    a suction part formed in said container member so as to extend outward through said container member and to be connected to a urine suction unit provided externally of said container member;
    a liquid-pervious sheet covering said opening of said container member, wherein, in use, an amount of urine sucked into said container member through said liquid-pervious sheet under a negative pressure generated by said urine suction unit is evacuated out from said container member via said suction part under said negative pressure;
    an electrical sensor adapted to be interposed between the wearer's skin and said liquid-pervious sheet so as to detect a urination by said wearer;
    a spacer sheet having a thickness of at least 0.7 mm and including a plurality of through-holes each having a diameter of at least 2 mm, wherein said spacer sheet is substantially incompressible in a thickness direction thereof; and
    a liquid-pervious filter sheet,
    wherein
    said container member is a hollow structure having a length direction, a width direction and a thickness direction which are orthogonal one to another, and comprises a bottom and a peripheral wall rising in the thickness direction from said bottom so that said peripheral wall surrounds said bottom,
    an upper edge of said peripheral wall defines said opening, said liquid-pervious sheet is attached to said upper edge and thereby said container member cooperates with said liquid-pervious sheet to form a urine suction space, said suction part has a urine suction port opening toward said urine suction space and a urine evacuation port opening toward the exterior of said urine suction space, said container member further comprises at least one rib positioned in a vicinity of and opposite to said urine suction port to prevent the liquid-pervious sheet from choking up said urine suction port, said at least one rib extends inwardly directly from a peripheral edge of said container member toward the urine suction port, said electrical sensor is at least partially covered by the liquid-pervious filter sheet to prevent solid content of bodily discharges from coming in contact with said electrical sensor, and said spacer sheet is interposed between said electrical sensor and said liquid-pervious filter sheet.

* * * * *